United States Patent [19]

Goidl et al.

[11] Patent Number: 4,814,350

[45] Date of Patent: Mar. 21, 1989

[54] METHOD OF TREATING DIABETES WITH 5-[1-HYDROXY-2-(ISOPROPYLAMINO)E-THYL]ANTHRANILONITRILE

[75] Inventors: Jo A. Goidl, Spring Valley, N.Y.; Thomas H. Claus, Montvale, N.J.

[73] Assignee: American Cyanamid Company, Stamford, Conn.

[21] Appl. No.: 905,606

[22] Filed: Sep. 10, 1986

[51] Int. Cl.$^4$ ............................................. A61K 31/275
[52] U.S. Cl. ..................................... 514/524; 514/866
[58] Field of Search ................................ 514/524, 866

[56] References Cited

U.S. PATENT DOCUMENTS 4,407,819 10/1983 Kiernan et al. ..................... 514/524

Primary Examiner—Frederick E. Waddell
Attorney, Agent, or Firm—Edward A. Conroy, Jr.

[57] ABSTRACT

This disclosure describes pharmaceutical compositions of matter containing 5-[1-hydroxy-2-(isopropylamino)ethyl]anthranilonitrile and the method of treating diabetes therewith.

1 Claim, No Drawings

METHOD OF TREATING DIABETES WITH 5-[1-HYDROXY-2-(ISOPROPYLAMINO)ETHYL]ANTHRANILONITRILE

BACKGROUND OF THE INVENTION

This invention relates to a method of treating diabetes and/or hyperglycemia in warm-blooded animals using the compound 5-[1-hydroxy-2-(isopropylamino)ethyl]anthranilonitrile, having the structure:

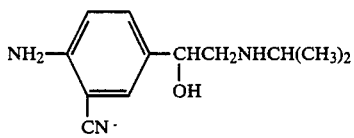

as well as pharmacologically acceptable acid-addition salts thereof.

The compound 5-[1-hydroxy-2-(isopropylamino)ethyl]anthranilonitrile is disclosed and claimed in German Pat. No. 2,261,914, together with methods for its preparation and stated utility for enhancing blood circulation and as bronchodilator, analgesic, sedative, antipyretic, antiphlogistic and antitussive agent in warm-blooded animals.

Its utility for enhancing the growth rate of meat-producing animals and/or improving the efficiency of feed utilization thereby is disclosed in U.S. Pat. No. 4,404,222 and its utility for increasing lean meat deposition and or improving lean meat to fat ratio in animals is disclosed in U.S. Pat. No. 4,407,819.

However, none of the above disclosures indicate or suggest that 5-[1-hydroxy-2-(ispropylamino)ethyl]anthranilonitrile, its derivatives, salts or congeners would be useful for the treatment of diabetes or hyperglycemia.

DESCRIPTION OF THE INVENTION

The disease diabetes mellitus is characterized by metabolic defects in the production and utilization of glucose which results in the failure to maintain appropriate blood sugar levels. The result of this defect is elevated blood glucose or hyperglycemia. Research on the treatment of diabetes has centered on attempts to normalize fasting and postprandial blood glucose levels. Treatments have included parenteral administration of exogenous insulin, oral administration of drugs, and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated, levels of insulin and appears to be the result of the inability of tissues to respond appropriately to insulin.

The compound of the present invention and the pharmacologically active acid-addition salts thereof, effectively lower blood glucose levels when administered orally to genetic strains of hyperglycemic mice which are animal models of type II diabetes. The exact mechanism by which they act is not known and the invention should not be construed as limited to any particular mechanism of action. As effective hypoglycemic agents, these compounds are useful for the treatment of hyperglycemia in type II diabetes.

This invention is also concerned with pharmaceutical compositions containing the above-described compounds.

The compounds of this invention may be prepared according to the reaction scheme shown and described below:

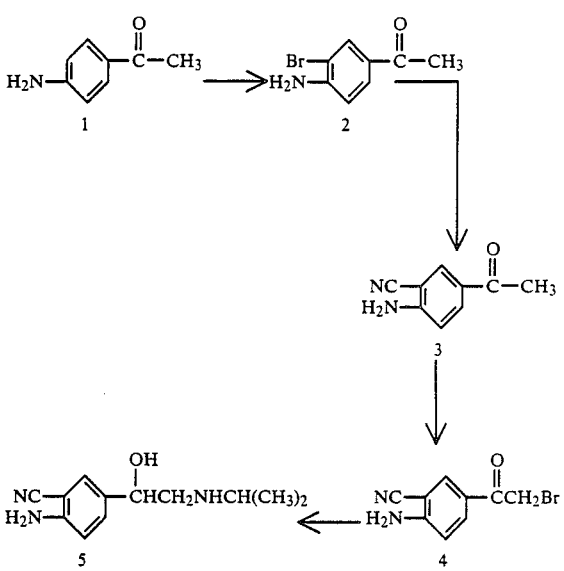

Bromination of 4'-aminoacetophenone 1 using N-bromosuccinimide gives 4'-amino-3'-bromoacetophenone 2, which is then reacted with cuprous cyanide, giving 5-acetylanthranilonitrile 3. Reaction of 3 with cupric bromide gives 5-bromoacetylanthranilonitrile 4 which is then reacted with isopropylamine, followed by in situ reduction using sodium borohydride, giving 5-[1-hydroxy-2-(isopropylamino)ethyl]anthranilonitrile 5.

Acid addition salts of 5 are derived by conventional treatment with various inorganic and organic acids such as oleic acid.

The compound 5-[1-hydroxy-2-(isopropylamino)ethyl]anthranilonitrile was tested for hypoglycemic activity according to the following procedure.

Obese mice [C57 B1/6J (ob/ob)], their lean littermates (ob/+or +/+) and diabetic mice [C57 B1/Ks (db/db)]and their non-diabetic littermates (db/+or +/+) were obtained from Jackson Laboratories, Bar Harbor, Me. Obese mice were 8 weeks of age and diabetic mice were 9 weeks of age at the start of the test.

The compound 5-[1-hydroxy-2-(isopropylamino)ethyl]anthranilonitrile was dissolved in methanol, mixed with powdered Purina rodent chow on a weight of compound to weight of chow basis and thoroughly dried.

Groups of 4 control mice received vehicle (methanol) treated chow.

Groups of 4 test mice were fed ad libitum for one month and food consumption was measured daily (on week days) by weighing the food bins before and after the addition of fresh chow. Thus a 40 g mouse fed the test compound at a concentration of 0.02% of the diet would receive a dose of 20 mg/kg/day if it ate 4 g of chow per day.

Blood samples were collected before the first treatment and once at the end of each week of treatment by retro-orbital puncture using heparinized capillary tubes. Plasma was separated by centrifugation in a Beckman microfuge for 5 minutes. Plasma glucose concentrations were determined with the Beckman Glucose Analyzer which uses a glucose oxidase method.

The results of this test appear in Table I.

TABLE I

Effect of 5-[1-hydroxy-2-(isopropylamino)ethyl]anthranilonitrile on blood glucose

| Type of Mice | Dose % (w/w) | Blood Glucose Levels in mg/100 ml ± S.E. Week | | | | |
|---|---|---|---|---|---|---|
| | | 0 | 1 | 2 | 3 | 4 |
| ob/ob | Control | 227.5 ± 21 | 188.0 ± 8 | 202.5 ± 8 | 185.0 ± 8 | 224.8 ± 14 |
| | .02 | 219.0 ± 17 | 117.5 ± 7 | 122.5 ± 4 | 112.3 ± 7 | 107.5 ± 11@ |
| | .002 | 226.3 ± 18 | 132.5 ± 9 | 143.3 ± 7 | 145.3 ± 2 | 137.8 ± 7@ |
| | .0005 | 223.5 ± 13 | 172.5 ± 12 | 135.8 ± 13 | 162.0 ± 24 | 152.3 ± 6* |
| | .0002 | 229.3 ± 18 | 212.3 ± 27 | 140.0 ± 2 | 173.0 ± 12 | 158.3 ± 4* |
| ob/+ | Control | | 167.8 ± 6 | 163.3 ± 8 | 186.8 ± 14 | 195.3 ± 14 |
| | .02 | | 139.8 ± 4@ | 133.0 ± 4* | 138.0 ± 10* | 137.0 ± 8* |
| | .002 | | 152.0 ± 10 | 134.5 ± 10 | 137.5 ± 4* | 112.0 ± 16* |
| | .0005 | | 129.0 ± 4@ | 139.3 ± 4 | 130.5 ± 3* | 127.3 ± 6* |
| | .0002 | | 141.3 ± 4* | 143.5 ± 2 | 137.8 ± 4* | 133.8 ± 10* |
| db/db | Control | 285.3 ± 33 | 253.0 ± 37 | 321.8 ± 27 | 392.3 ± 44 | 604.8 ± 16 |
| | .02 | 265.8 ± 35 | 117.8 ± 9* | 124.0 ± 3* | 121.0 ± 6* | 130.5 ± 8@ |
| | .002 | 272.5 ± 22 | 129.5 ± 7* | 124.3 ± 10@ | 146.0 ± 7* | 183.3 ± 35@ |
| | .0005 | 339.3 ± 50 | 175.5 ± 23* | 163.8 ± 21@ | 189.8 ± 27* | 256.0 ± 83@ |
| | .0002 | 326.5 ± 64 | 221.3 ± 61 | 207.0 ± 64@ | 204.0 ± 57* | 293.8 ± 98@ |
| db/+ | Control | | 146.8 ± 10 | 148.8 ± 10 | 159.5 ± 6 | 157.5 ± 8 |
| | .02 | | 142.0 ± 6 | 133.5 ± 9 | 129.8 ± 6* | 123.3 ± 12 |
| | .002 | | 138.3 ± 6 | 140.0 ± 3 | 138.0 ± 4* | 127.0 ± 8* |
| | .0005 | | 129.0 ± 2 | 138.0 ± 5 | 132.3 ± 6* | 138.0 ± 6 |
| | .0002 | | 180.0 ± 12 | 131.0 ± 3 | 136.3 ± 1* | 132.0 ± 6 |

@= Statistically significant reduction in blood glucose concentration from control at the same study time $p < 0.01$.
*= Statistically significant reduction in blood glucose concentration from control at the same study time $p < 0.05$.

When the compounds are employed for the above utility, they may be combined with one or more pharmaceutically acceptable carriers, e.g., solvents, diluents and the like, and be administered orally in such forms as tablets, capsules, dispersible powders, granules, or suspensions containing, for example, from about 0.5 to 5% of suspending agent, and elixirs containing, for example, from about 20 to 50% ethanol and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained whent the compounds of the invention are administered at a daily dosage of from about 1 milligrams to about 10 milligrams per kilogram of animal body weight, preferably given in divided doses two to four times a day, or in sustained release form. For most large mammals, the total daily dosage is from about 35 milligrams to about 1,400 milligrams preferably from about 35 milligrams to 500 milligrams. Dosage forms suitable for internal use comprise from about 35 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally. Solid carriers include dicalcium phosphate, microcrystalline cellulose, and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral administration of the compounds is preferred.

The invention will be more fully described in conjuction with the following specific examples which are not to be construed as limiting the scope of the invention.

EXAMPLE 1

4'-Amino-3'-bromoacetophenone

To a stirred solution of 48.96 g 4'-aminoacetophenone in 490 ml of toluene was added 64.5 g of solid N-bromosuccinimide in portions over 30 minutes, such that the temperature did not exceed 40° C. Fifteen minutes later, the warm solution was washed with water, dried with sodium sulfate and evaporated in vacuo, giving a dark brown oil, which became crystalline when treated with 20 ml of ether and 80 ml of hexane. The brown crystals were collected, giving 70.5 g of the desired compound, mp 59°–62° C.

EXAMPLE 2

5-Acetylanthranilonitrile

A stirred mixture of 35.5 g of 4'-amino-3'bromoacetophenone, 17.8 g of cuprous cyanide and 180 ml of dry dimethylformamide was heated at reflux, under nitrogen for 6 hours. After cooling, the mixture was treated with 180 ml of a solution of ferric chloride (prepared from 400 g of ferric chloride hexahydrate, 100 ml of concentrated hydrochloric acid and 600 ml of water) and stirred for 20 minutes at 60°–70° C. A 500 ml portion of water and 400 ml of dichloromethane were added. To facilitate phase separation, the mixture was filtered and then the filtrate was extracted with two 400 ml portions of dichlorometbane. The organic extracts were combined, washed with 200 ml of water and 200 ml of saturated sodium bicarbonate solution and the solvent removed in vacuo at 80° C. The residue was evaporated twice from 100 ml portions of toluene, giving a yellow solid, which was crystallized from ethanol, giving 14.35 g of the desired compound, mp 155°–159° C.

EXAMPLE 3

5-Bromoacetylanthranilonitrile

A stirred mixture of 1 g of 5-acetylanthranilonitrile, 10 ml of tetrahydrofuran and 2.8 g of finely ground cupric bromide was heated at reflux for 1 hour and 35 minutes, then filtered while hot and the cake washed with 20 ml of tetrahydrofuran. The combined filtrate and wash was evaporated, then the residue was slurried with 5 ml of dichloromethane and filtered, giving 1.2 g of the desired compound, mp 162°–165° C.

EXAMPLE 4

5-1-Hydroxy-2-(isopropylamino)ethyl]anthranilonitrile

A mixture of 122.5 ml of isopropylamine and 245 ml of ethanol was cooled to 7° C. under nitrogen. Ice bath cooling was maintained as 406 g of 5-bromoacetylanthranilonitrile was added at once to the mixture with stirring. An exotherm raised the temperature to 23° C. and a homogeneous brown solution resulted. When the temperature fell to 20° C., cooling was terminated and the mixture was stirred for 10 minutes, then cooled to 10° C. A 147 g portion of sodium borohydride was added during a 30 minute period. Toward the end of this addition the temperature was allowed to reach 20°–22° C. The cooling bath was removed and the temperature reached 31° C. After 3.5 hours, the temperature had fallen below 28° C. and the mixture was cooled to 10° C. Three liters of water were added and the mixture was again cooled to below 10° C.

The solid was collected, washed with water and air dried (130.6 g), then divided into three approximately equal portions. Each portion was dissolved in 2.2 liters of hot acetone, decolorized with activated charcoal, the solvent removed in vacuo and hexane added. The resulting combined product (102.3 g) was further purified by dissolving in hot methanol and decolorizing with activated charcoal, giving 91.7 g of the desired compound as a light yellow solid, mp 160°–165° C.

EXAMPLE 5

5-[1-Hydroxy-2-(isopropylamino)ethyl]-anthranilonitrile, oleate

To a warm solution of 0.5 g of 5-[1-hydroxy-2(isopropylamino)ethyl]anthranilonitrile in 40 ml of methanol was added, with swirling a solution of 0.6 g of oleic acid in 20 ml of methanol. The solvent was removed in vacuo, giving 1.1 g of the desired product as a yellow gummy solid, mp 74°–78° C.

We claim:

1. A method of treating diabetes mellitus and/or hyperglycemia in a mammal in need of such treatment, which comprises administering to said mammal an effective antidiabetic or hypoglycemic amount of 5-[1-hydroxy-2-(isopropylamino)ethyl]anthranilonitrile or a pharmacologically acceptable acid addition salt thereof.

* * * * *